US012285900B1

(12) United States Patent
Lindsey et al.

(10) Patent No.: US 12,285,900 B1
(45) Date of Patent: Apr. 29, 2025

(54) CONTROLLED TUBING EXPANSION AND SURFACE ENGINEERING

(71) Applicant: ZEUS COMPANY INC., Orangeburg, SC (US)

(72) Inventors: James M. Lindsey, Lexington, SC (US); Bruce L. Anneaux, Lexington, SC (US); Zahidul Wahab, Orangeburg, SC (US)

(73) Assignee: Zeus Company LLC, Orangeburg, SC (US)

( * ) Notice: Subject to any disclaimer, the term of this patent is extended or adjusted under 35 U.S.C. 154(b) by 4 days.

(21) Appl. No.: 17/574,846

(22) Filed: Jan. 13, 2022

Related U.S. Application Data

(63) Continuation of application No. 16/153,222, filed on Oct. 5, 2018, now abandoned.

(60) Provisional application No. 62/569,075, filed on Oct. 6, 2017.

(51) Int. Cl.
| | |
|---|---|
| *A61F 2/91* | (2013.01) |
| *A61L 29/08* | (2006.01) |
| *A61L 31/10* | (2006.01) |
| *B29C 49/00* | (2006.01) |
| *A61M 25/00* | (2006.01) |
| *A61M 25/10* | (2013.01) |
| *B29L 31/00* | (2006.01) |

(52) U.S. Cl.
CPC .............. *B29C 49/071* (2022.05); *A61F 2/91* (2013.01); *A61L 29/085* (2013.01); *A61L 31/10* (2013.01); *A61F 2240/001* (2013.01); *A61M 25/0009* (2013.01); *A61M 25/104* (2013.01); *B29C 2949/08* (2022.05); *B29L 2031/7534* (2013.01)

(58) Field of Classification Search
CPC .. A61F 2/91; A61F 2/915; A61F 2002/91558; A61F 2002/91533; A61F 2002/91525; A61L 31/10; A61L 29/085
See application file for complete search history.

(56) References Cited

U.S. PATENT DOCUMENTS 5,741,327 A * 4/1998 Frantzen .................. A61F 2/91
606/198
2016/0228267 A1 * 8/2016 Pacetti .................... A61L 31/04

* cited by examiner

*Primary Examiner* — Vi X Nguyen
(74) *Attorney, Agent, or Firm* — Jessica L. Gorczynski; Womble Bond Dickinson (US) LLP

(57) ABSTRACT

The disclosure provides methods for expanding a polymeric tube using one or more deformable members. The methods can involve disposing the polymeric tube within the one or more deformable members and radially deforming the polymeric tube and the one or more deformable members. The rate of deformation of the polymeric tube and/or the extent of deformation of the one or more polymeric tubes can advantageously be controlled along one or more axes by at least one of the one or more deformable members.

24 Claims, 9 Drawing Sheets

CONTROLLED TUBING EXPANSION AND SURFACE ENGINEERING

CROSS-REFERENCE TO RELATED APPLICATIONS

The present application is a continuation of U.S. patent application Ser. No. 16/153,222, filed Oct. 5, 2018; which application claims priority to United States Provisional Patent Application No. 62/569,075, filed Oct. 6, 2017. Both applications are hereby incorporated herein by reference in their entirety.

FIELD OF THE INVENTION

The present invention relates primarily to methods of manufacturing and processing radially expanded tubes. Tubes for a variety of end applications are also described herein.

BACKGROUND OF THE INVENTION

Stents are generally cylindrically shaped devices often used in the treatment of arterial disease. Arterial disease involves the deposition of lipids within an artery and subsequent plaque formation along the arterial wall. These plaque lesions may be soft or become hard and calcified and over time reduce the luminal space within the vessel, a process known as stenosis. To treat stenosis, stents are commonly deployed at the treatment site serving to maintain patency of the lumen of the diseased segment of the vessel. Stents must have adequate radial strength to provide the vessel with adequate radial support to maintain vessel patency.

Stents are commonly manufactured by laser cutting a tube to into a radially expandable geometry comprising interconnected structural elements or struts. During conventional deployment as with an angioplasty balloon catheter, the stent struts undergo high localized deformation requiring the material from which the stents are manufactured to be highly deformable while maintaining high strength and rigidity (e.g., the material must exhibit high toughness).

Stents are constructed of many materials such as metals and polymers, including bioabsorbable polymers. Metals generally have higher strength and stiffness compared to polymers. To produce a polymeric stent with a radial strength comparable to a metallic stent of comparable dimensions, the polymeric material from which the stent is manufactured is processed to induce molecular orientation in the polymeric material. The molecularly oriented polymeric material exhibits improved properties such as high strength and toughness compared to polymeric material that has not been processed to induce molecular orientation.

There are a number of methods known in the art to induce molecular orientation in a polymeric material in a tubular form. Conventional methods employ annular expansion of extruded or molded polymeric tubes as in blow molding. In conventional blow molding, an extruded polymeric tube is disposed within a mold, heated to a rubbery state, and pressurized to expand the tube into the mold. In some methods, the extruded polymeric tube is also stretched in the machine direction by applying tension. The machine direction stretching is completed prior to or during the annular expansion. The final expanded tube geometry is generally determined by the geometry of the mold and the process parameters such as temperature and pressure. The properties of the final expanded tube are generally determined by process parameters such as annular expansion ratio, annular expansion rate, machine direction stretch ratio, machine direction stretch rate, temperature, and pressure. In many clinical treatment applications, the stent is temporarily required, for example, to maintain patency during a critical healing phase or to deliver an active agent or a drug to a target site. Therefore, stents fabricated from bioabsorbable materials such as bioabsorbable polymers are able to meet this additional clinical requirement since they can be completely absorbed after their clinical utility has ended. Polymeric biodegradable tubes generally comprise one or more biodegradable polymers, e.g., including, but not limited to, poly(L-lactide) (PLLA), poly(D-lactide) (PDLA), poly(D, L-lactide) (PDLLA), poly(ε-caprolactone) (PCL), polyglycolic acid (PGA), poly(para-dioxanone) (PDO), poly(trimethylene carbonate) (PTMC), poly(hydroxybutyrate), poly (hydroxyvalerate), poly(tetramethyl carbonate), and copolymers, blends, and derivatives thereof. Selection of the polymer or polymers to produce a polymeric bioabsorbable tubes can have implications on both the biocompatibility/toxicity properties of the resulting tube and/or any device or component made therefrom and the physical/mechanical properties of the resulting tube and/or any device or component made therefrom, e.g., rate of degradation, strength (e.g., radial strength), and recoil rate.

Angioplasty balloons used in percutaneous transluminal coronary angioplasty (PTCA) procedures for the treatment of arterial disease are produced using similar blow molding processes. High-pressure, non-complaint balloons require properties such as high strength and low elongation which are achieved via the molecular orientation induced during the expansion/blowing/deformation process. It is of clinical advantage for a PTCA balloons to have uniform wall thickness for the proper (e.g., uniform) inflation during a clinical procedure. It is also of clinical advantage for PTCA balloons to have thin walls so that the balloon can have a low navigation profile (e.g., a small profile for improved delivery to treatment sites) and a low crossing profile (e.g., a small profile for passing through/crossing a diseased site/lesion).

Expanded polymeric tubes used to produce stents/scaffolds typically exhibit smooth surfaces (e.g. inner and outer diameters) in accordance with their typical manufacturing processes. For example, tubing extrusion processes typically produce tubing with smooth inner and outer diameter surfaces based on optimal polymer flow conditions (e.g. low shear stress). Tubing used as a precursor/input to a radial expansion process will typically maintain its smooth inner and outer diameters throughout the radial expansion process. The inner diameter surface remains smooth due to its remaining free from contacting any other material surfaces during the radial expansion process. The outer diameter surface of the radially expanded tube remains smooth due to its coming in intimate contact with a mold whose inner surface could also be characterized as smooth.

SUMMARY OF THE INVENTION

Annular/radial expansion processes currently used to manufacture polymeric tubes for bioabsorbable stent/scaffold applications and PTCA balloons are limited as to the ability to control the rate and extent of deformation of the polymeric tubes during the expansion process. This limitation is due in large part to the polymeric "input" tubes being substantially unsupported/unconstrained during the majority of the expansion/deformation process (e.g., until the "input" comes into contact with a stationary mold surface). In typical expansion processes such as blow molding, stretch-blow molding, and injection-blow molding, the control of the deformation rate of the polymeric input tube/preform/parison is limited primarily to the gage pressure differential employed, the rate of gage pressure change, and the inherent properties of the "input" tubing inasmuch as such properties affect the tubing response to applied forces at certain temperatures. Additionally, the extent of expansion/deformation along certain axes (e.g., the axial axis) is difficult to control in typical expansion processes. This is due in large part to the tendency of a substantially unsupported/unconstrained, substantially isotropic polymeric material to deform along multiple axes (e.g., axial and radial axes) in response to a gage pressure differential at typical process temperatures. Accordingly, in a typical tubing expansion process in which an input tube is expanded radially into a mold (e.g., a cylindrical mold), it is difficult to control and/or limit the deformation of the tube in the axial direction resulting in a greater potential for non-uniform properties including dimensional, mechanical and thermal properties, especially where long lengths of expanded tubes are desired.

Supporting/constraining the outer diameter/outer surface of a polymer tube during the expansion process as outlined herein can provide for better control of expansion/deformation and more uniform expansion/deformation. This can be achieved, in general, by disposing a polymer "input" tube within at least one deformable member and expanding/deforming the polymer tube along with the deformable member. The deformable member can act to restrain/limit the deformation of the polymer tube by limiting the rate and/or extent of deformation of the outer surface of the polymer tube to essentially that of the inner surface the deformable member. This limiting effect can generally be achieved by, although not limited to, the selection of a deformable member with properties such that the rate and/or extent of expansion of the deformable member is less than the rate and/or extent of expansion of the polymer tube along one or more axes under similar expansion conditions (e.g., temperature, pressure, forces, etc.). Multiple deformable members can be used to control the expansion of a polymer tube in sequential steps by positioning the polymer tube and deformable members in a nested fashion (e.g., one within another) and expanding the polymer tube into a first/innermost deformable member, expanding polymer tube and first deformable member into a second deformable member, expanding the polymer tube, first deformable member and second deformable member into a third deformable member and so forth. The rate and extent of expansion of each step can be controlled by selecting certain sizes/dimensions (e.g., inner diameter, outer diameter, wall thickness) and properties (e.g., radial strength, radial modulus, radial stress-strain profile) of the deformable members. Additionally, various process steps and/or process parameters, including but not limited to, temperature changes, pressure changes, dwell times, axial stretch, and axial relaxation can be introduced/changed during, prior to, or after at any of the steps. Axial stretch and relaxation steps can be applied to the polymer tube, one or more of the deformable members, or both.

According to the present disclosure, deformable members can also be positioned inside the polymer tube and can be used to control the rate and/or extent of deformation of the polymer tube. The deformable members inside the polymer tube can be used to expand the polymer tube into one or more deformable members, into a mold, or into both. The internal pressure required to radially expand an innermost deformable member can be applied directly to the deformable member wherein the deformable member comprises a closed system (e.g., a sealed tube or a balloon capable of being sufficiently pressurized to achieve expansion of the polymer tube). The internal pressure required to radially expand a deformable member that does not comprise a closed system (e.g., cannot be sufficiently pressurized to achieve expansion of the outer adjacent polymer tube due to characteristics such as porosity) can be applied via a deformable member that does comprise a closed system (e.g. a sealed tube or a balloon) that is positioned inside the deformable member that does not comprise a closed system.

Other methods for expanding/deforming polymer tubes, including but not limited to die drawing and mandrel drawing, can be improved according to the present disclosure by using deformable members to affect/control the rate and or extent of deformation of a polymer tube. Die drawing is a process wherein a tube is forced through a die (e.g., a metal ring), typically at temperatures suitable for inducing molecular orientation, in order to deform the tube based on the dimensions of the die. Mandrel drawing is a process wherein a tube is forced over a mandrel (e.g., a tapered metal rod), typically at temperatures suitable for inducing molecular orientation, in order to deform the tube based on the dimensions of the mandrel. One or more deformable members positioned inside or outside of one or more polymer tubes can limit the extent of deformation along one or more axes (e.g., radial and/or axial axes) during such deformation processes resulting in one or more polymer tubes with one or more of more uniform dimensions and more uniform properties than one or more polymer tubes deformed by such processes without the connection with one or more deformable members.

Annular/radial expansion processes currently used to manufacture polymeric tubes for bioabsorbable stent/scaffold applications are limited as to the ability to control the surface properties/texture/pattern of the radially expanded tubes and result in predominantly smooth inner and outer diameter surfaces. The use of deformable members as outlined above with particular properties, morphologies, geometries, and/or surface characteristics can be used to produce expanded polymeric tubes with non-smooth inner and/or outer diameter surfaces, especially those featuring application-specific surface textures/patterns/characteristics, which will find utility in a number of applications due to their advantageously providing properties, characteristics, and/or features including but not limited to (i) increased surface area for adhesion of coatings, (ii) increased surface area for adhesion of drugs (e.g. anti-proliferative drugs), (iii) increased surface area for the binding of molecules (e.g. antibodies), (iv) increased surface area for the bonding of adjacent polymeric and or non-polymeric layers/surfaces, (v) increased surface area and/or ideal patterning for cellular adhesion/attachment, (vi) increased surface area and/or ideal patterning for cellular proliferation, (vii) increased surface area and/or ideal patterning for cellular differentiation, (viii) features capable of acting as reservoirs, (ix) features capable of influencing flow properties of adjacent fluid flow fields (e.g. blood flow), (x) increased hydrophilicity or hydrophobicity, and (xi) increased or decreased surface energy.

The nature of the expanded tube produced according the methods described herein is inherently advantageous in a number of aspects, including:
  1. Dimensional uniformity;
  2. Property uniformity;
  3. Improved mechanical properties;
  4. Improved thermal properties; and
  5. Macro-and-micro patterned/textured surfaces.

Polymeric tubes produced according to the methods described herein are well suited for being converted (e.g., by laser cutting) into bioabsorbable stents/scaffolds for the treatment of vascular disease including but not limited to coronary artery disease and peripheral artery disease. The sizes of stents provided according to certain embodiments of the disclosed method can vary, and may be suitably designed for one or more specific applications. For example, in some embodiments, the length, L of the stent may be from about 20 mm to about 200 mm. For example, for some applications, the stent may have a length, L, of from about 40 mm to 100 mm or any value between, for example, at least about 50 mm, 60 mm, 70 mm, 80 mm, or 90 mm. In some applications, the stent may have a length, L, of from about 25 mm to 150 mm or any value between, for example at least about 50 mm, 75 mm, 100 mm or 125 mm. The stent may also be longer or shorter than these exemplary values in other stent applications. Likewise, in some embodiments, the strut thickness of the stent may be from about 0.7 mm to about 0.4 mm. For example, for some applications, the stent may have a strut thickness of from about 0.08 mm to 0.15 mm or any value between, for example, at least about 0.09 mm, 0.1 mm, 0.12 mm, 0.13 mm, or 0.14 mm. In some applications, the stent may have a strut thickness of from about 0.15 mm to 0.4 mm or any value between, for example at least about 0.2 mm, 0.25 mm, 0.3 mm or 0.35 mm. The stent may also have a strut thickness greater than or less than these exemplary values in other stent applications. Likewise the stent may be formed with a variety of diameters. In some embodiments the midbody diameter of the stent (the diameter of the stent at a point equidistant from each end) may be from about 1.5 mm to about 40 mm, such as a midbody inside diameter of about 2.5 mm to 16 mm or any distance within this range such as between about 3 mm to 14 mm or between about 5 mm to about 10 mm.

Polymeric tubes and/or balloons produced according to the methods described herein are well suited for use in PTCA, stent/scaffold delivery, and drug delivery (e.g., drug coated stents/scaffolds or drug coated balloons).

In one aspect, the present disclosure provides a method, comprising: disposing one or more polymeric tubes within one or more deformable members; and radially deforming the one or more polymeric tubes and at least one of the one or more deformable members, wherein one or more of a rate of deformation of the one or more polymeric tubes and an extent of deformation of the one or more polymeric tubes is controlled based at least in part on at least one of the one or more deformable members.

In some embodiments, the method further comprises disposing the one or more polymeric tubes and one or more deformable members within a mold, and radially deforming the one or more polymeric tubes and the one or more deformable members within the mold until at least one of the one or more deformable members contacts the inner surface of the mold. In some embodiments, the method of claim 1, wherein at least one of the one or more deformable members is removed from the one or more radially deformed polymeric tubes after the radial deformation of the one or more polymeric tubes or during the radial deformation of the one or more polymeric tubes.

The method, in certain embodiments, further comprises selecting the one or more deformable members based at least in part on a property of at least one of the one or more deformable members. Selection of at least one of the one or more deformable members can be, for example, based at least in part on one or more of a desired extent of radial deformation of the one or more polymeric tubes or a desired extent of axial deformation of the one or more polymeric tubes. In some such embodiments, the one or more of a desired extent of radial deformation of the one or more polymeric tubes or a desired extent axial deformation of the one or more polymeric tubes are based at least in part on one or more properties of the one or more polymeric tubes before deformation of the one or more polymeric tubes, or one or more properties of the one or more polymeric tubes after deformation of the one or more polymeric tubes. In some embodiments, at least one of the one or more deformable members is selected based on one or more of the following properties of the at least one of the one or more deformable members: i. a mechanical property; ii. a degree of anisotropy; iii. a chemical property; iv. a frictional property; v. a surface property; and vi. a topographical property.

In certain embodiments, at least one of the one or more deformable members is anisotropic. The term "anisotropic," as used herein, is intended to mean having a property or characteristic that has a different value when measured in different directions. A degree of anisotropy of the at least of the one or more deformable members is, in some embodiments, with respect to at least one of (i) a characteristic of a stress-strain relationship; and (ii) morphological characteristic of the at least of the one or more deformable members. In certain embodiments, the characteristic of the stress-strain relationship comprises one or more of a stress at a particular strain value, a strain at a particular stress value, a slope of a stress-strain curve at a particular strain value, a slope of a stress strain curve at a particular stress value, strain at break, modulus of elasticity, yield stress, and ultimate strength. In certain embodiments, the morphological characteristic of the at least of the one or more deformable members comprises one or more of a pore size, a node size, a node orientation, an internodal distance, a fibril size, a fibril orientation, and an inter fibril distance In some embodiments, at least one of the one or more deformable members comprises a polymeric deformable member. For example, at least one of the one or more deformable members can comprise a polymeric tubular deformable member. In some such embodiments, the polymeric tubular deformable member is selected based at least in part on a representative value corresponding to one or more of: i. an inner diameter of the polymeric tubular deformable member; ii. an outer diameter of the polymeric tubular deformable member; iii. a wall thickness of the polymeric tubular deformable member; iv. a density of the polymeric tubular deformable member; v. a porosity of the polymeric tubular deformable member; vi. a node-fibril morphology of the polymeric tubular deformable member; vii. an internodal distance of the polymeric tubular deformable member, viii. a compressibility of the polymeric tubular deformable member, and ix. a degree of anisotropy of the polymeric tubular deformable member. Each of these characteristics may have some degree of variability and this "representative value" can, in some embodiments, be the average, median, range, or some other statistical measure of that characteristic or property. In certain embodiments, the polymeric tubular deformable member comprises expanded polytetrafluoroethylene (ePTFE).

In some embodiments, one or more of a rate of deformation of at least one of the one or more polymeric tubes and an amount of deformation of at least one of the one or more polymeric tubes is controlled based at least in part on one or more of (i) controlling one or more of an internal pressure of at least one of the one or more polymeric tubes and a pressure ramp rate of the at least one of the one or more polymeric tubes, and (ii) selecting the at least one of the one or more deformable members based at least in part on an internal force or an internal pressure that, at a predetermined temperature, is sufficient to radially deform the at least one of the one or more deformable members by a predetermined amount or at a predetermined rate. In certain embodiments, the internal force or internal pressure is applied to the one or more deformable members by the at least one of the one or more polymeric tubes, the internal force or internal pressure being applied in response to the radial deformation of the at least one of the one or more polymeric tubes. In certain embodiments, the internal force or the internal pressure sufficient to radially deform the at least one of the one or more deformable members by the predetermined amount or at the predetermined rate is controlled based at least in part on selecting the at least one of the one or more deformable members based at least in part on a representative value corresponding to one or more of: i. a wall thickness of the at least one of the one or more deformable members; ii. a cross-sectional area of the at least one of the one or more deformable members; iii. a radial strength of the at least one of the one or more deformable members; iv. a radial modulus of the at least one of the one or more deformable members; and v. an axial tension of the at least one of the one or more deformable members. Each of these characteristics may have some degree of variability and this "representative value" can, in some embodiments, be the average, median, range, or some other statistical measure of that characteristic or property. The axial tension of at least one of the one or more deformable members in certain embodiments is controlled based at least in part by controlling an axial deformation of at least one of the one or more deformable members.

In some embodiments, the one or more of the rate of deformation of at least one of the one or more polymeric tubes, and the extent of deformation of at least one of the one or more polymeric tubes, is controlled based at least in part on one or more stress-strain properties along one or more axes of at least one of the one or more deformable members. In some embodiments, the one or more of the rate of deformation of at least one of the one or more polymeric tubes, and the extent of deformation of at least one of the one or more polymeric tubes, is controlled in continuous or non-continuous manner. In some embodiments, a rate of deformation of at least one of the one or more polymeric tubes expanded in connection with at least one of the one or more deformable members is lower along one or more axes than a rate of deformation of a same one or more polymeric tubes expanded without the connection with at least one of the one or more deformable members. In some embodiments, an extent of deformation of at least one of one or more polymeric tubes expanded in connection with at least one of the one or more deformable members is higher along one or more axes than an extent of deformation of a same one or more polymeric tubes expanded without the connection with at least one of the one or more deformable members.

In certain embodiments of the disclosed method, the variation in one or more of: i. a wall thickness of the one or more expanded polymeric tubes, ii. an inner diameter of the one or more expanded polymeric tubes, iii. an outer diameter of the one or more expanded polymeric tubes, iv. a mechanical property of the one or more expanded polymeric tubes, v. a chemical property of the one or more expanded polymeric tubes, vi. a thermal property of the one or more expanded polymeric tubes, and vii. a thermodynamic property of the one or more expanded polymeric tubes, is lower along one or more of a circumferential direction, radial direction, and axial direction of at least one of the one or more expanded polymeric tubes expanded in connection with the one or more deformable members, compared to a same one or more expanded polymeric tubes expanded without the connection with the one or more deformable members. In certain embodiments of the disclosed method, one or more of: i. a mechanical property of the one or more expanded polymeric tubes, ii. a chemical property of the one or more expanded polymeric tubes, iii. a thermal property of the one or more expanded polymeric tubes, and iv. a thermodynamic property of the one or more expanded polymeric tubes, is improved along one or more of a circumferential direction, radial direction, and axial direction of a least one of the one or more expanded polymeric tubes expanded in connection with the one or more deformable members, compared to a same one or more expanded polymeric tubes expanded without the connection with the one or more deformable members.

In certain embodiments, the one or more polymeric tubes is disposed with a plurality of deformable members. In some such embodiments, at least one of the plurality of deformable members is disposed at least partially within an area defined by an inner diameter surface of another one of the plurality of deformable members. In some such embodiments, at least one of the plurality of deformable members is nested within at least one or more other deformable members of the plurality of deformable members.

In another aspect of the disclosure is provided a method, comprising: disposing one or more deformable members within one or more polymer tubes; and radially deforming at least one of the one or more polymeric tubes in connection with radially deforming at least one of the one or more deformable members, wherein one or more of a rate of deformation of the one or more polymeric tubes and an extent of deformation of the one or more polymeric tubes is controlled based at least in part on at least one of the one or more deformable members. The at least one of the one or more polymeric tubes and the at least one of the one or more deformable members are, in some embodiments, disposed within one or more additional deformable members prior to the radial deformation step.

In certain embodiments of the methods disclosed herein, the one or more of the rate of deformation of at least one of the one or more polymeric tubes, and the extent of deformation of at least one of the one or more polymeric tubes, is controlled along one or more axes of the one or more polymeric tubes. In certain embodiments of the methods disclosed herein, at least one of a part of an inner surface of the one or more polymeric tubes and a part of an outer surface of the one or more polymeric tubes is changed in response to the radial deformation of the one or more polymeric tubes. For example, in some embodiments, a texture or topography of the part of the inner surface of the one or more polymeric tubes or the part of the outer surface of the one or more polymeric tubes is changed. In certain embodiments, the at least one of the part of the inner surface of the one or more polymeric tubes and the part of the outer surface of the one or more polymeric tubes is changed based at least in part on one or more characteristics of the one or more deformable members.

In another aspect is provided a method, comprising: disposing one or more polymeric tubes within one or more deformable members; and radially deforming the one or more polymeric tubes and at least one of the one or more deformable members, wherein at least one of a part of an inner surface of the one or more polymeric tubes and a part of an outer surface of the one or more polymeric tubes is changed based at least in part on one or more characteristics of the one or more deformable members.

In a further aspect is provided a method, comprising: disposing one or more deformable members within one or more polymer tubes; and radially deforming at least one of the one or more polymeric tubes in connection with radially deforming at least one of the one or more deformable members, wherein at least one of the part of an inner surface of the one or more polymeric tubes and the part of an outer surface of the one or more polymeric tubes is changed based at least in part on one or more characteristics of the one or more deformable members.

In certain embodiments of the methods disclosed herein, at least one of the one or more deformable members comprises expanded polytetrafluoroethylene (ePTFE). In certain embodiments, at least one of the one or more polymeric tubes comprise one or more of a polyester, a poly α-hydroxy ester, a polyetherester, a polylactide, a polycaprolactone, a polyglycolide; a poly(dioxanone); a poly trimethylene carbonate; a poly(hydroxybutyrate); a poly(anhydride); an aliphatic polycarbonate; a poly(orthoester); a poly(amino acid); a poly(ethylene oxide); a poly (ethylene glycol); a polyphosphazene, a polyvinyl alcohol, a poly(tetrafluoroethylene), an expanded poly(tetrafluoroethylene), a fluorinated ethylene propylene, a polyaryletherketone, a polyamide, polyethylene terephthalate, and stereoisomers, or copolymers or blends thereof.

The disclosure further provides an expanded polymeric tube prepared according to any of the methods disclosed herein. The disclosure further provides medical devices and products comprising or prepared from such expanded polymeric tubes.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise. Other aspects and advantages of the present invention will become apparent from the following.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

Figure 1:
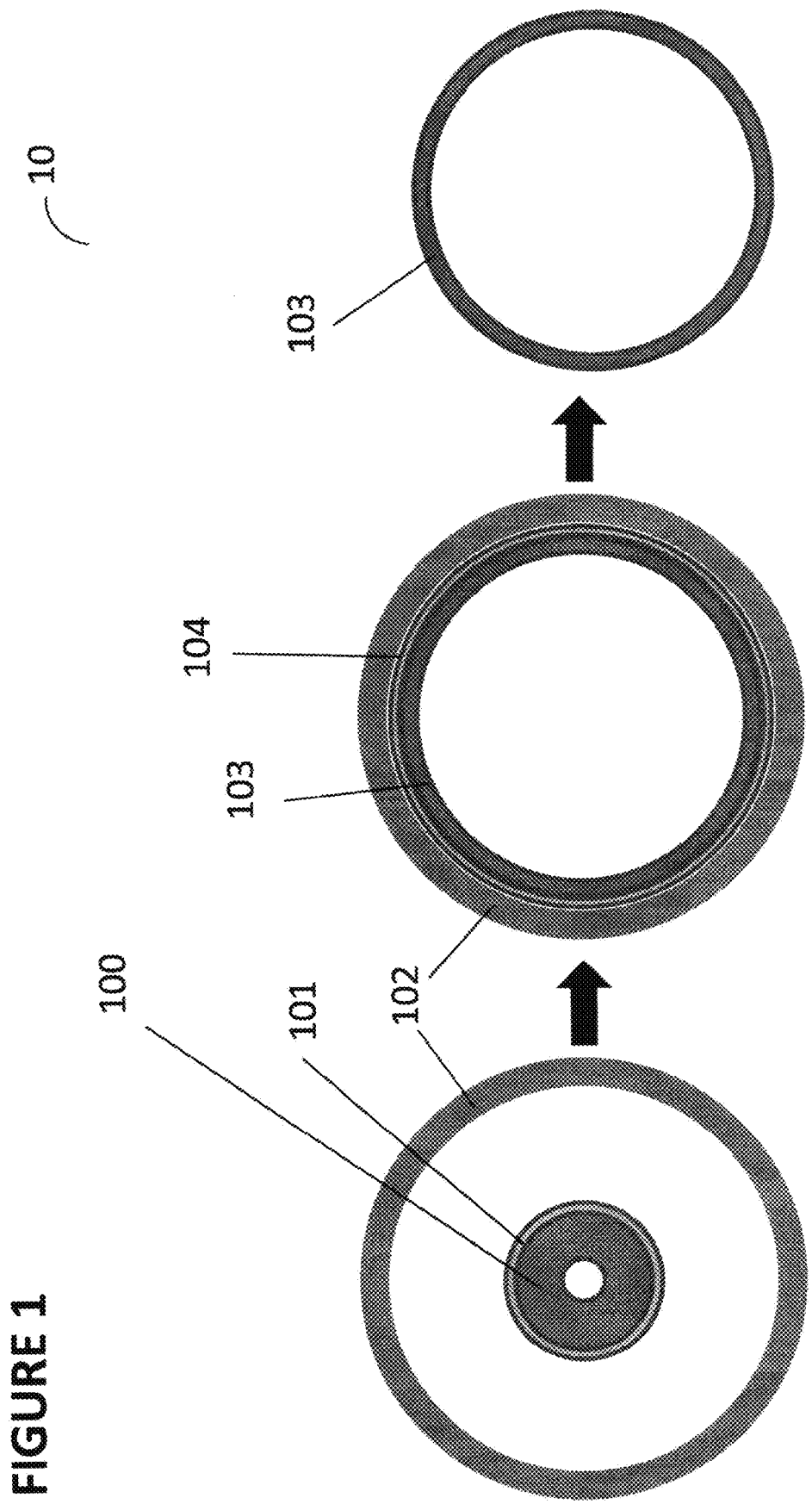
FIG. 1 provides a schematic overview of the method disclosed herein.

The disclosure relates generally to methods for preparing radially and axially expanded/radially and axially molecularly oriented polymeric tubes, and in particular, to methods for preparing such tubes with one or more of highly uniform dimensions and properties, enhanced properties, and enhanced surface features/patterns/textures via the use of deformable members. An exemplary, schematic overview of the method 10 outlined herein is provided in FIG. 1, with specific exemplary methods represented in other figures provided herewith. The disclosed methods generally involve the radial expansion of a polymeric input tube, for example polymeric input tube 100 as illustrated in FIG. 1., with the rate and/or extent of deformation of the polymeric input tube 100 being controlled along the radial/circumferential axis and/or the axial axis by deformable member 101 as both the input tube 100 and the deformable member 101 are radially expanded into non-deformable mold 102. The radially expanded tube 103 and radially expanded deformable member 104 are removed from the non-deformable mold 102. The radially expanded deformable member 104 is removed from the radially expanded tube 103. The radially expanded tube 103 exhibits outer diameter surface characteristics directly influenced by the surface characteristics of the inner diameter surface of the radially expanded deformable member 104. The total degree of radial expansion of input tube 100 and the size (e.g. outer diameter and wall thickness) of the radially expanded tube 103 is affected by the size (e.g. inner diameter) of the non-deformable mold 102 and the final size (e.g. wall thickness) of the deformable member 104. The final size of the deformable member can be influenced by various means such as temperature and pressure especially in the case where the deformable member is compressible. The axial deformation upon radial expansion of input tube 100 is limited to approximately the axial deformation upon radial expansion of the deformable member 101. The input tube 100 can be axially deformed before, during, or after the radial expansion step. The deformable member 101 can be axially deformed before, during, or after the radial expansion step.

Figure 2:
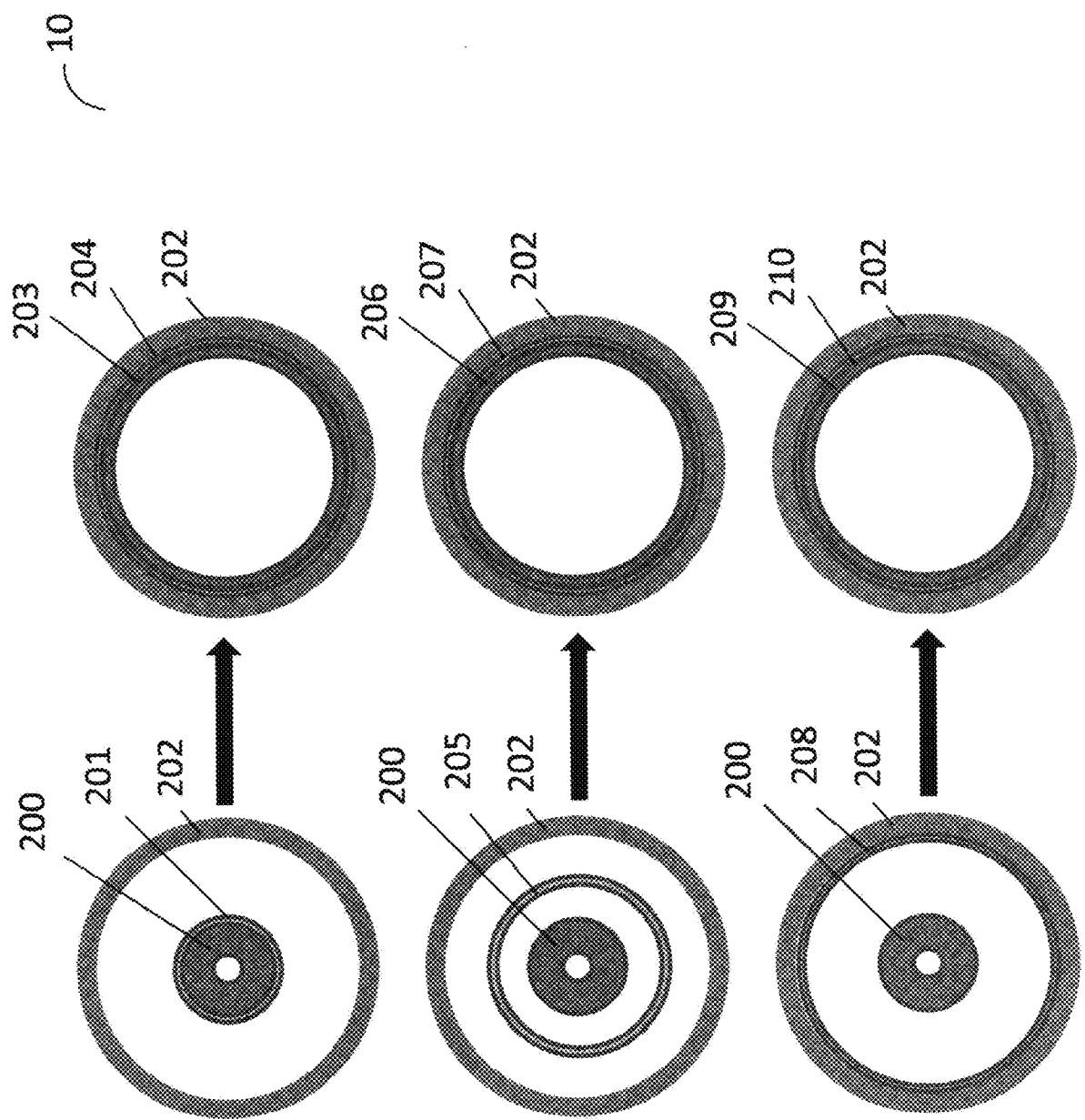
FIG. 2 provides an exemplary representation of a preferred embodiment of the method disclosed herein.

As illustrated in FIG. 2., deformable members of different sizes, for example deformable members 201, 205, and 208, are used to control the radial expansion of polymer input tube 200 in producing radially expanded tubes 203, 206, and 209 respectively. The amount of radial expansion of the input tube 200 prior to coming into full radial contact with the deformable members 201, 205, and 208 is affected by the size (e.g. inner diameter) of the deformable members 201, 205, and 208. The outer diameter surface characteristics of radially expanded tubes 203, 206, and 209 are directly influenced by the inner diameter surface characteristics of radially expanded deformable members 204, 207, and 210. The inner diameter surface characteristics of radially expanded deformable members 204, 207, and 210 are controlled by the pre-selected inner diameter surface characteristics of deformable members 201, 205, and 208 and the pre-determined extent of radial expansion of the deformable members 201, 205, and 208 employed in the radial expansion of input tube 200. Also as illustrated in FIG. 2., in the case of deformable member 208, the deformable member can essentially function as a non-deformable member when the distance between the deformable member and the non-deformable mold 202 is minimized especially to the extent that the deformable member is non-compressible. As such the essentially non-deformable deformable member 208 is used primarily to control the outer diameter surface characteristics of the radially expanded tube 210.

Figure 3:
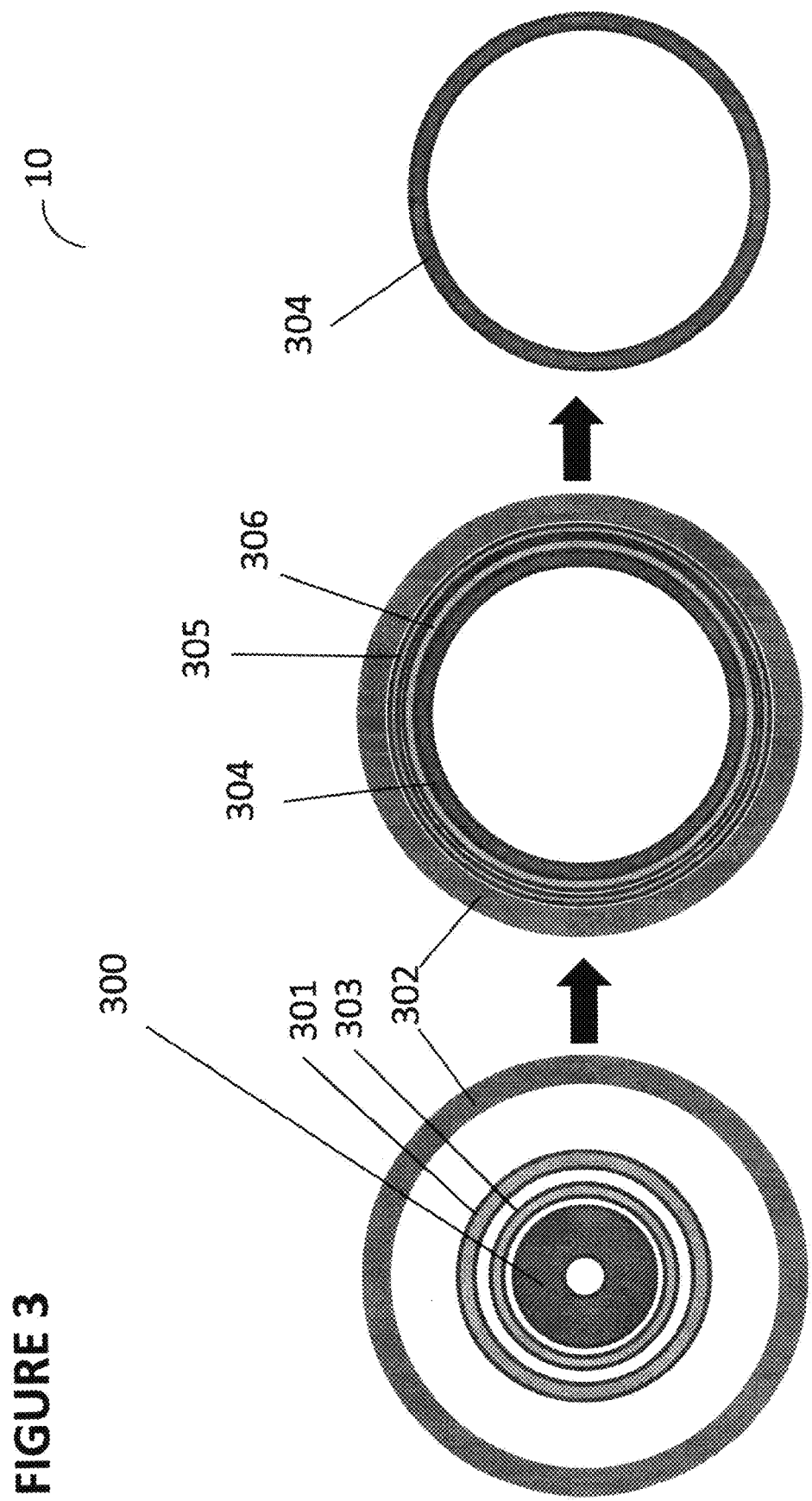
FIG. 3 provides an exemplary representation of a preferred embodiment of the method disclosed herein.

As illustrated in FIG. 3., more than one deformable member, for example deformable members 301 and 303, are used to control the radial expansion of polymer input tube 300 in producing the radially expanded tube 304. The innermost deformable member 303 is used to further control the radial expansion of the polymer input tube 300 (e.g. in conjunction with deformable member 301), and/or used to modify the outer diameter surface characteristics of radially expanded tube 304. In the case where the outermost deformable member 301 is sufficient to control the radial expansion of polymer tube 304, the innermost deformable member 303 acts predominately to modify the outer diameter surface characteristics of radially expanded tube 304. This modification of the outer diameter surface characteristics ranges from forming particular non-smooth surface characteristic to the maintenance of a smooth surface in the case where a non-smooth surface characteristic is not desired. Therefore, using more than one deformable member allows for multiple advantageous aspects of the disclosed method herein to be realized independently or in conjunction.

Figure 4:
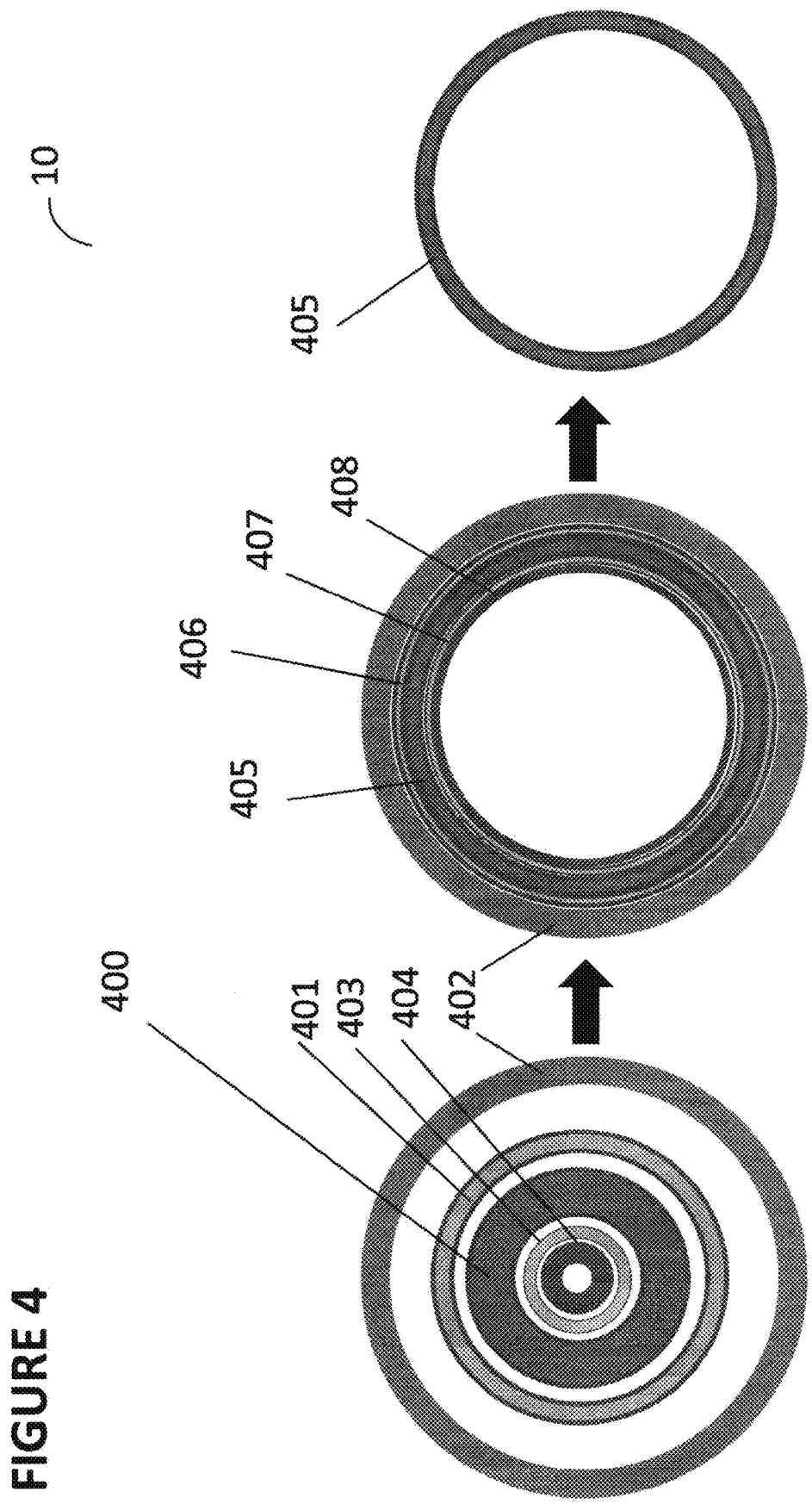
FIG. 4 provides an exemplary representation of a preferred embodiment of the method disclosed herein.

As illustrated in FIG. 4., deformable members are positioned both inside and outside of polymer input tube 400 to the control the radial expansion of polymer input tube 400 in producing the radially expanded tube 405 and/or to modify the inner and outer diameter surface characteristics of radially expanded tube 405. The innermost deformable member 404 acts as a pressurizeable member and as such provides the radial force required to radially expand deformable member 403, polymer input tube 400, and deformable member 401 into the non-deformable mold 402. As a result, the radially expanded tube 405 has outer diameter surface characteristics produced in connection with the outer deformable member 401 and inner diameter surface characteristics produced in connection with the inner deformable member 403. In general, a requirement for a deformable member suitable for various embodiments of the method disclosed herein is that the deformable member be capable of being radially expanded under the general expansion conditions of the polymer "input" tubing. However, a high degree of control of the expansion of the polymer "input" tubing can be achieved by selecting deformable members with select attributes including, but not limited to, select physical/mechanical properties, morphological properties, and chemical properties. By selecting particular materials with particular attributes, the following attributes of the deformable members can be employed to various degrees, in various levels/ratios, and/or in various amounts:

Physical/Mechanical Properties:
   a. Radial and/or axial stress-strain profile (e.g., the radial and/or axial deformation (strain) response to an applied load (pressure/stress) can include responses including but not limited to elastic, elastic-plastic, strain hardening, and strain softening).
   b. Radial and/or axial modulus of elasticity
   c. Radial and/or axial yield stress/strength
   d. Radial and/or axial ultimate strength
   e. Degree of anisotropy (e.g., can range from zero (isotropic) to a positive amount)
   f. Poisson's ratio (e.g., can range from a negative value to 0.5)
   g. Density
   h. Porosity
   i. Pore size
   j. Permeability (e.g. air flow)
   k. Internodal distance
   l. Fibril size
   m. Node size
   n. Fibril orientation (e.g., uniaxial, biaxial)
   o. Sintering level
   p. Fiber size
   q. Basis weight
   r. Tear strength
   s. Compressive strength
   t. Compressive modulus
   u. Coefficient of friction
   v. Coefficient of thermal conductivity
   w. Coefficient of thermal expansion
   x. Surface energy
   y. Surface topography
   z. Melting temperature
   aa. Glass transition temperature
   bb. Crystallinity
   cc. Molecular weight
   dd. Dimensions (e.g., thickness)

Morphological Properties:
   a. Node-fibril structure (e.g., ePTFE)
   b. Open-cell pore (e.g., open-cell foams)
   c. Closed-cell pore (e.g., closed-cell foams)
   d. Non-woven structure (e.g., electrospun, melt blown, spunbond, SMS)
   e. Molecular/crystallite orientation Chemical Properties
   a. Chemical inertness
   b. Chemical stability
   c. Thermal stability The geometrical structure of the deformable members can also be selected/controlled in order to control/affect one or more properties of the deformable members. In certain embodiments, the following geometries and associated attributes of the deformable members can be employed:

Geometries:
a. Continuous-wall tube or rolled sheet/film (e.g., extruded tube or sheet/film): inner diameter, outer diameter, wall thickness, length
b. Braided tube or rolled flat braid: inner diameter, outer diameter, wall thickness, length, braid construction, number of braid ends, braid angle, braid coverage, braid density, pick distance, yarn/filament profile/shape
c. Woven tube or rolled woven sheet/film: inner diameter, outer diameter, wall thickness, length, weave construction/type, weave coverage, weave density, yarn/filament profile/shape
d. Knitted tube or rolled knitted sheet/film: inner diameter, outer diameter, wall thickness, length, knit construction/type, knit coverage, knit density, yarn/filament profile/shape
e. Laser-cut, radially expandable tube or rolled laser cut or slit-and-stretched sheet/film: inner diameter, outer diameter, wall thickness, length, strut angle, strut width, strut thickness, strand width and diamond dimensions in the case of slit-and-stretched sheet/film

TABLE 1

Process Enhancements Afforded by Various Types of Deformable Members

|  | ePTFE Deformable Member | Braided Deformable Member | Foam Deformable Member | Solid Polymeric Deformable Member |
|---|---|---|---|---|
| Controlled radial expansion rate | Y | Y | Y | Y |
| Limited axial extension | Y | Y | Y | Y |
| Controlled axial extension | Y | Y | Y | Y |
| Axial relaxation upon radial expansion | Y | Y | N | N |
| Pressure differential uniformity | Y | Y | Y | N |
| Patterning | Y | Y | Y | Y |
| Special macro-patterning | N | Y | Y | N |
| Special micro-patterning | Y | Y | Y | N |
| Special nano-patterning | Y | N | Y | N |

The control of the expansion of a polymeric "input" tube can be enhanced by the selection of a deformable member with certain properties based on a combination of the properties of the "input" tube and the desired outcome of the expansion process (e.g., uniform wall thickness, high tensile strength, high expansion ratio, reduced mechanical and thermal property variation, limited axial deformation, etc.).

In a preferred embodiment, a tubular deformable member comprises an extruded ePTFE tube and exhibits:
1. A radial and axial stress-strain profile that is largely independent of temperature within a temperature range optimal for the expansion and molecular orientation of a polymeric "input" tube.
2. Anisotropic properties with a higher modulus, higher yield stress, higher strength, etc. in the axial direction than in the radial direction.
3. A size and extent of radial expansion sufficient to achieve the desired extent of radial expansion of the input tube at optimal expansion conditions for the input tube.
4. Axial shortening upon radial expansion.
5. A mode of radial/circumferential and axial deformation wherein the deformation is uniformly distributed along each respective axis as opposed to being localized (e.g., necking).
6. A radial yield force/stress greater than, less than or equal to the radial yield force/stress of the polymeric "input" tube at a given temperature.
7. An axial yield force/stress greater than the axial yield force/stress of the polymeric "input" tube at a given temperature.
8. An air/gas permeability that allows for pressure uniformity across a wall/thickness of the deformable member.

Using a deformable member with the aforementioned properties, an "input" tube can be radially expanded into the deformable member at a pressure wherein the deformable member will also be radially expanded. The input tube and deformable member will then therefore be radially expanded simultaneously into a mold. Because of the sufficient contact between the input tube and the deformable member, and/or because of the greater axial yield force/stress of the deformable member compared to the axial yield force/stress of the input tube, any axial deformation of the input tube will be substantially limited to the axial deformation of the deformable member. Because the deformable member contracts axially when radially expanded, the input tube will also contract axially when radially expanded rather than having the tendency to elongate axially as in the case of substantially unsupported/unconstrained expansion. Because the inherent mode of radial/circumferential deformation of the deformable member is not localized but rather distributed evenly along the radial/circumferential direction, and because the deformation of the deformable member is minimally affected by temperature within the process temperature range, any undesirable localized/concentrated regions of radial/circumferential deformation of the deformable member, and thus the input tube, can be minimized. The expanded tube and deformable member can then be removed from the mold and the deformable member removed from the expanded tube. The result is an expanded tube with a highly uniform average wall thickness in the axial direction and a highly uniform wall thickness in the radial/circumferential direction.

In another preferred embodiment, a tubular deformable member comprises an extruded expanded-PTFE (ePTFE) tube and exhibits:
1. A radial and axial stress-strain profile that is substantially independent of temperature within a temperature range optimal for the expansion and molecular orientation of a polymeric "input" tube.
2. Anisotropic properties with a higher modulus, higher yield stress, higher strength, etc. in the axial direction than in the radial direction.
3. A size and extent of radial expansion allowing for the desired extent of radial expansion of the input tube at desired expansion conditions for the input tube.
4. Axial shortening upon radial expansion.
5. A mode of radial/circumferential and axial deformation wherein the deformation is uniformly distributed along each respective axis as opposed to being localized (e.g., necking).
6. A radial yield force/stress, either inherently or by influence of an applied axial force, greater than the radial yield force/stress of the polymeric "input" tube at a given temperature.
7. An axial yield force/stress greater than the axial yield force/stress of the polymeric "input" tube at a given temperature.
8. An air/gas permeability that allows for pressure uniformity across a wall/thickness of the deformable member.

Using a deformable member with one or more of the aforementioned properties, an "input" tube can be radially expanded into the deformable member at a pressure wherein the deformable member is not significantly deformed (e.g., wherein the deformable member limits the deformation of the input tube). The input tube and deformable member can then be stretched in the axial direction. This stretching can be substantially simultaneous. Because the resistance to deformation of the deformable member creates an opposing force to that of the internal pressure of the expanded input tube, the frictional force between the input tube and the deformable member is enhanced by the resulting normal force. With the frictional force, the outer diameter/surface of the input tube maintains strong contact with the inner/surface of the deformable member, and as such, the axial stretch of the input tube is limited substantially to the axial stretch of the deformable member. Because the inherent mode of axial deformation of the deformable member is not localized but rather distributed evenly along its length, and because the deformation of the deformable member is minimally affected by temperature within the process temperature range (e.g., it would otherwise be susceptible to uneven deformation due to any uneven temperatures), any undesirable localized/concentrated regions of axial deformation along the length of the deformable member, and thus the input tube, can be minimized. After the axial stretching step, the pressure can be increased to a value greater than the radial yield stress of the deformable member, and the input tube and deformable member can be expanded radially into a mold. Because the inherent mode of radial/circumferential deformation of the deformable member is not localized but rather distributed evenly along the radial/circumferential direction, and because the deformation of the deformable member is minimally affected by temperature within the process temperature range, any undesirable localized/concentrated regions of radial/circumferential deformation of the deformable member, and thus the input tube, can be minimized. Also, because of the axial deformation attributes of the deformable member noted above, the axial deformation of the input tube during the radial expansion step is also limited to the axial deformation of the deformable member. Because the deformable member contracts axially when radially expanded, the input tube will also contract axially when radially expanded rather than having the tendency to elongate axially as in the case of substantially unsupported/unconstrained expansion. The expanded tube and deformable member can then be removed from the mold and the deformable member removed from the expanded tube. The result is an expanded tube with a highly uniform average wall thickness in the axial direction and a highly uniform wall thickness in the radial/circumferential direction.

In another preferred embodiment, a tubular deformable member comprises a braided polymeric or metallic tube and exhibits:
1. A radial and axial stress-strain profile that is largely independent of temperature within a temperature range optimal for the expansion and molecular orientation of a polymeric "input" tube.
2. A size and extent of radial expansion sufficient to achieve the desired extent of radial expansion of the input tube at optimal expansion conditions for the input tube.
3. A braid configuration such that the inner diameter can be controlled by controlling the axial length (e.g., the inner diameter can be fixed by fixing the axial length or can be increased or decreased by decreasing or increasing the axial length, respectively).
4. Axial shortening upon radial expansion.
5. A mode of radial/circumferential and axial deformation wherein the deformation is uniformly distributed along each respective axis as opposed to being localized (e.g., necking).
6. A radial yield force/stress, either inherently or by influence of an applied axial force, greater than the radial yield force/stress of the polymeric "input" tube at a given temperature.
7. An axial yield force/stress greater than the axial yield force/stress of the polymeric "input" tube at a given temperature.

Using a deformable member with the aforementioned properties and with a fixed/constrained axial length (e.g., by clamping), an "input" tube can be radially expanded into the deformable member at a pressure wherein the deformable member is not significantly deformed (e.g., wherein the deformable member limits the deformation of the input tube). The length of the deformable member can be allowed to shorten in a controlled fashion with the driving force for shortening being the outward radial force from pressurized input tube due to the braid construction. The control of the shortening of the deformable member allows for the control of the radial expansion of the input as it substantially limits the expansion of the input tube to the expansion of the inner diameter of the deformable member. The rate of shortening of the deformable member can be controlled. The shortening of the deformable member can be controlled in multiple fashions including but not limited a linear fashion, step-wise fashion, and an exponential fashion. Because of the sufficient contact between the input tube and the deformable member, and because of the greater axial yield force/stress of the deformable member compared to the axial yield force/stress of the input tube, any axial deformation of the input tube will be limited to that of the deformable member. Because the deformable member contracts axially when radially expanded, the input tube will also contract axially when radially expanded rather than having the tendency to elongate axially as in the case of substantially unsupported/unconstrained expansion. Because the inherent mode of radial/circumferential deformation of the deformable member is not localized but rather distributed evenly along the radial/circumferential direction, and/or because the deformation of the deformable member is minimally affected by temperature within the process temperature range, any undesirable localized/concentrated regions of radial/circumferential deformation of the deformable member, and thus the input tube, can be minimized. The expanded tube and deformable member can then be removed from the mold and the deformable member removed from the expanded tube. The expanded tube can exhibit a highly uniform average wall thickness in the axial direction and/or a highly uniform wall thickness in the radial/circumferential direction.

In another preferred embodiment, a tubular deformable member comprises a foam tube and exhibits:
1. A radial compression stress-strain profile that is largely independent of temperature within a temperature range optimal for the expansion and molecular orientation of a polymeric "input" tube.
2. A size and extent of radial compression sufficient to achieve the desired extent of radial expansion of the input tube at optimal expansion conditions for the input tube.
3. Minimal axial change upon radial compression.
4. A mode of radial/circumferential and axial compression/deformation wherein the deformation is uniformly distributed along each respective axis as opposed to being localized (e.g., necking).
5. A radial compression yield force/stress greater than, less than or equal to the radial yield force/stress of the polymeric "input" tube at a given temperature.

Using a deformable member with the aforementioned properties, an "input" tube can be radially expanded into the deformable member at a pressure wherein the deformable member can be radially compressed against a mold. Because of the sufficient contact between the input tube and the deformable member, the deformable member can limit the rate and extent of both the axial and radial deformation of the input tube. The expanded tube and deformable member can then be removed from the mold and the deformable member removed from the expanded tube. The expanded tube can exhibit a highly uniform average wall thickness in the axial direction and/or a highly uniform wall thickness in the radial/circumferential direction.

In addition to the enhanced dimensional uniformity achieved by the embodiments disclosed above and herein, optimal and more uniform physical/mechanical, chemical, and thermal properties can also be achieved by employing the methods disclosed above and herein. Because of the reduced and more controlled rate of expansion/deformation along one or more axes, higher expansion/deformation ratios are able to be achieved. This is due to the lower stress in the polymer input tube during expansion/deformation resulting from the lower strain/deformation rates (e.g., the viscous response to deformation/strain). The lower stress can allow for a higher extent of deformation and a more optimal polymer morphology (e.g., optimal molecular orientation, crystallinity, crystallite size, etc.). This can lead to improved properties such as improved strength and toughness.

In the above embodiments, the desired properties of the ePTFE deformable members can be obtained by selecting or producing ePTFE tubing with the appropriate combination of physical properties (e.g., density, porosity, internodal distance, node size, fibril size, fibril orientation, molecular weight, crystallinity, sintering level, strength, elongation, stiffness, degree of anisotropy, Poisson's ratio, etc.) and dimensions (e.g., inner diameter, outer diameter, wall thickness, etc.). The desired properties of the braided deformable members can be obtained by selecting or producing braided deformable members with the appropriate combination of physical properties (e.g., braid construction, number of braid ends, braid angle, braid coverage, braid density, pick distance, yarn/filament size/profile/shape, molecular weight, crystallinity, sintering level, strength, elongation, stiffness, degree of anisotropy, Poisson's ratio, etc.) and dimensions (e.g., inner diameter, outer diameter, wall thickness, etc.). The desired properties of the foam deformable members can be obtained by selecting or producing foam deformable members with the appropriate combination of physical properties (e.g., density, porosity, pore size, pore orientation, molecular weight, crystallinity, sintering level, strength, elongation, stiffness, compression profile, degree of anisotropy, Poisson's ratio, etc.) and dimensions (e.g., inner diameter, outer diameter, wall thickness, etc.).

Materials/candidates suitable for continuous-wall, braided, woven, knitted, and/or non-woven deformable members include but are not limited to porous and/or non-porous fluoropolymers (e.g., PTFE, FEP, PFA, THV, PVDF, EFEP, and ETFE), polyolefins (e.g. HDPE, LDPE, LLDPE, UHMWPE, PP), polyesters (e.g., PET, PLA, PCL, PGA), polyketones (e.g., PEEK, PAEK), polyamides (e.g., nylon 6, nylon 12, and nylon 6/6), polyetheramides (e.g., Pebax), polyurethanes, polyethers, polyether-esters, polycarbonates, and polyimides, rubbers, elastomers, thermosets, ceramics, and metals. In a preferred embodiment, one or more deformable members comprise expanded polytetrafluorethylene (ePTFE). ePTFE is porous material typically exhibiting a node-fibril morphology that is produced by expanding/stretching PTFE along one or more axes. The structure of ePTFE is composed of a number of solid nodes interconnected by a matrix of very thin fibrils. The size of the node and fibrils and the spacing between nodes and fibrils can be manipulated during the manufacturing process.

Figure 5:
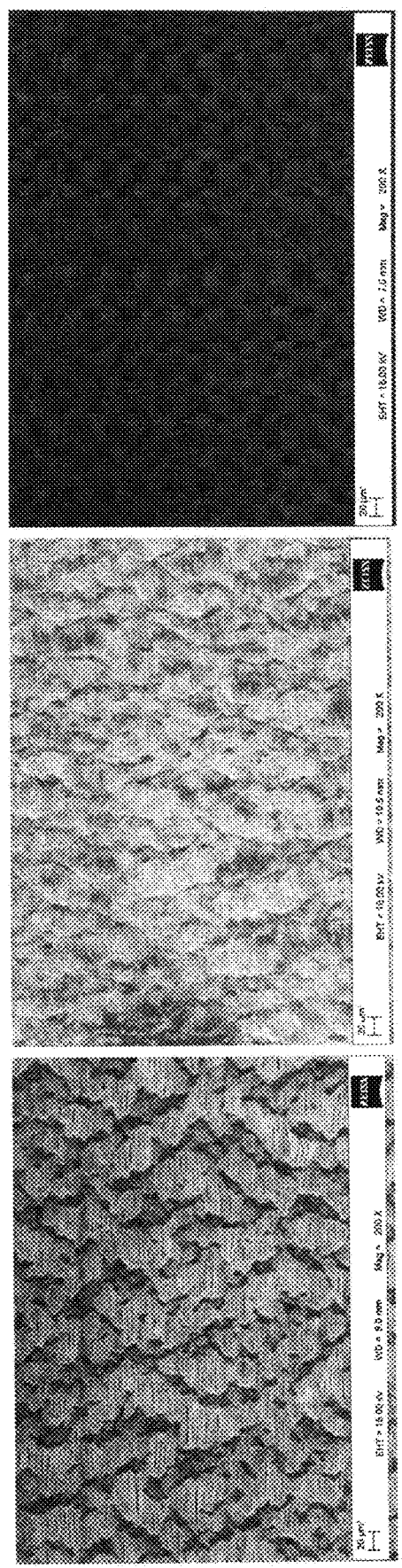
FIG. 5.: Scanning Electron Microscopy (SEM) (Zeiss EVO 40) images of a) an ePTFE deformable member with a density of approximately 0.58 g/cc and an average internodal distance of approximately 29 microns, b) the inner diameter surface of the ePTFE deformable member after use as a deformable member in the radial expansion of a PLLA tube, and c) the outer diameter surface of the radially expanded PLLA tube.
Figure 6:
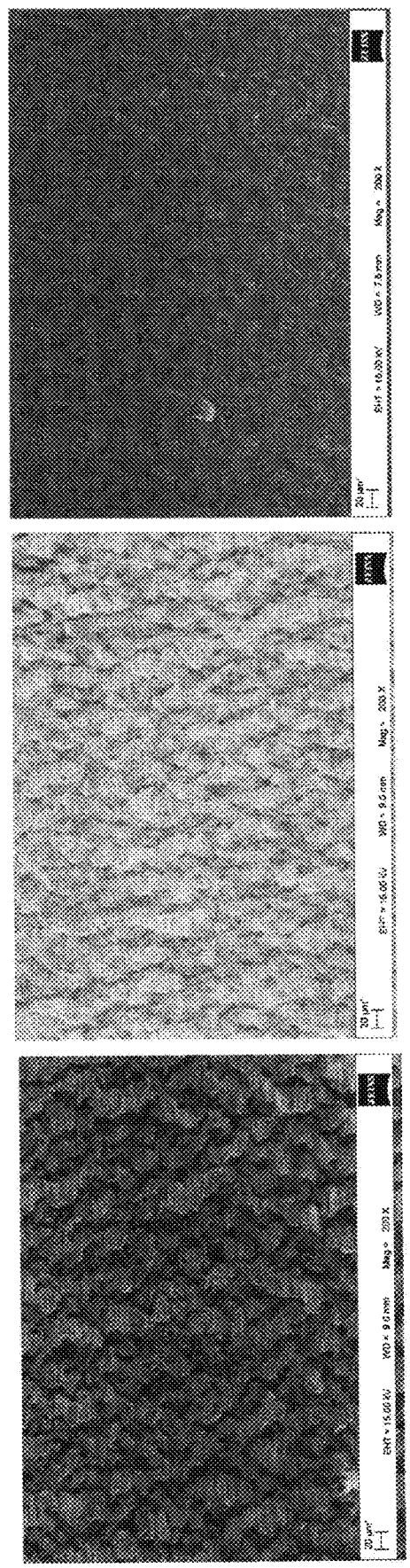
FIG. 6.: SEM images of a) an ePTFE deformable member with a density of approximately 0.75 g/cc and an average internodal distance of approximately 23 microns, b) the inner diameter surface of the ePTFE deformable member after use as a deformable member in the radial expansion of a PLLA tube, and c) the outer diameter surface of the radially expanded PLLA tube.
Figure 7:
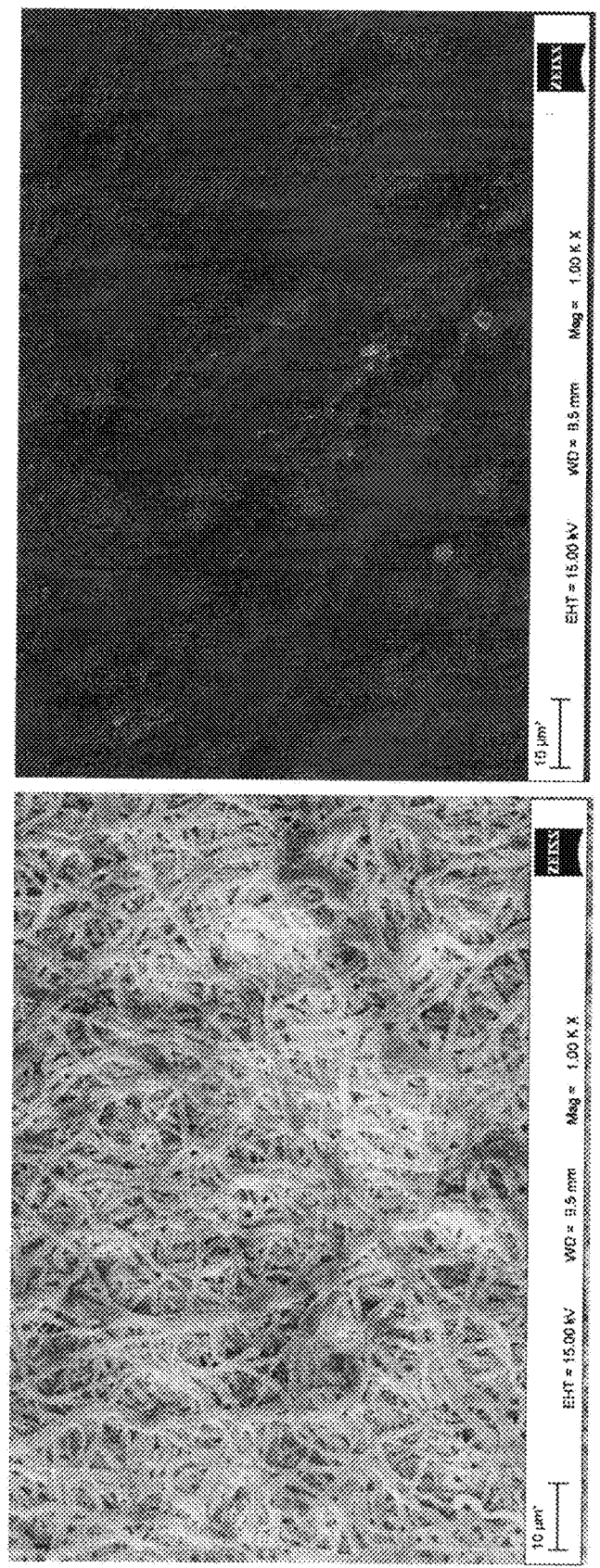
FIG. 7.: SEM images of a) the inner diameter surface of an electrospun PTFE deformable member after use as a deformable member in the radial expansion of a PLLA tube, and b) the outer diameter surface of the radially expanded PLLA tube.
Figure 8:
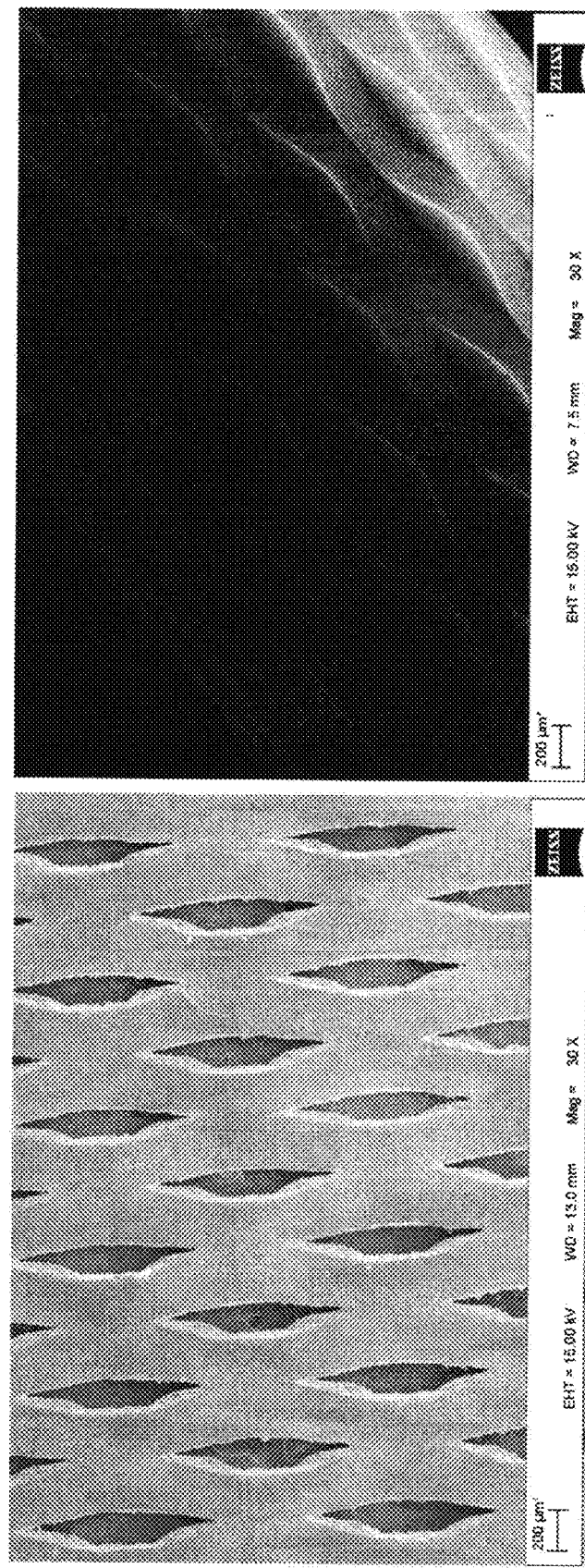
FIG. 8.: SEM images of a) the inner diameter surface of an "slit-and-stretch" PTFE deformable member after use as a deformable member in the radial expansion of a PLLA tube, and b) the outer diameter surface of the radially expanded PLLA tube.

The expansion of polymeric tubes using deformable members can also be used as a means to realize advantageous surface features/textures/attributes and/or surface properties of the expanded polymer tubes by impressing one or more of macro-surface features/attributes, micro-surface features/attributes, and nano-surface features/attributes of the deformable member onto/into one or more surfaces of the polymer tube (e.g., outer dimeter/surface and/or inner diameter/surface). Advantageous surface features/textures/attributes include but are not limited to impressions of the node-fibril surface of ePTFE (FIGS. 5 and 6), impressions from the non-woven patterns of electrospun PTFE (Zeus Industrial Products, Inc., USA) (FIG. 7), impressions from the patterns of "slit-and-stretch" PTFE (Dexmet Corporation, USA) (FIG. 8), impressions from the surfaces of open and/or closed cell foams, impressions from the various patterns of various braided, woven or knitted structures, and impressions from the non-woven patterns of other non-woven structures. Advantageous surface properties include but are not limited to improved biocompatibility, improved biological response, improved cellular attachment/adhesion, improved cellular proliferation, improved cellular migration, improved cellular differentiation, improved/increased surface area for improved adhesion of coatings, improved adhesion of drugs, improved adhesion of biologics (e.g., antibodies), improved/increased drug loading, and improved drug release. Applications particularly suited for such enhanced-surface polymeric tubing include but are not limited to bioabsorbable/bioresorbable vascular scaffolds, PTCA balloons, and drug-coated balloons.

The deformable member can be selected for its surface features in a pre-deformed state and/or its anticipated surface features in a post-deformed state. For example, the internodal distance, fibril length, fibril orientation, porosity, pore size, pore shape, node size, node shape, pore shape, and surface roughness, will in most cases vary between a pre-deformed state and post-deformed state. Accordingly, the selection of a certain pre-deformed surface feature/property of the deformable member can be selected based on an anticipated change in the surface feature/property according to a pre-determined extent of deformation of the deformable member under pre-determined process conditions including but not limited to temperature, pressure, pressure rate, and dwell time.

In a preferred embodiment, a deformable member comprising ePTFE having a density of 0.58 g/cc and an average internodal distance of approximately 29 microns is used to control the radial expansion of a PLLA tube and to create a pattern/texture on the outer surface of the radially expanded PLLA tube corresponding to the surface characteristics of the ePTFE including but not limited to the intermodal distance. After the radial expansion in connection with the deformable member, the PLLA tube exhibits a surface pattern/texture with an average repeating element spacing of approximately 34 microns, corresponding to the intermodal distance of the ePTFE deformable member.

In another preferred embodiment, a deformable member comprising ePTFE having a density of 0.75 g/cc and an average internodal distance of approximately 23 microns is used to control the radial expansion of a PLLA tube and to create a pattern/texture on the outer surface of the radially expanded PLLA tube corresponding to the surface characteristics of the ePTFE including but not limited to the intermodal distance. After the radial expansion in connection with the deformable member, the PLLA tube exhibits a surface pattern/texture with an average repeating element spacing of approximately 23 microns, corresponding to the intermodal distance of the ePTFE deformable member.

Multiple deformable members comprising the same or different materials, the same or different properties, and/or the same or different size can be combined and used in the expansion of a single polymeric input tube. The selection and combination of multiple deformable members can be used to further control the rate and/or extent of expansion and/or achieve a particular combination of the control of the rate and/or extent of expansion and an advantageous surface feature/texture/attribute/property. Multiple deformable members can be positioned such that the deformable members vary along the radial and or axial directions to afford control of various features, properties and/or dimensions that change along the radial and/or axial direction including but not limited to surface features/textures/attributes/properties, inner diameter, outer diameter, and wall thickness.

Deformable members, especially tubular ePTFE deformable members, can be especially useful in the expansion of long polymeric tubes as their limiting/controlling effect, especially in the axial direction, renders the expansion process less susceptible to uneven temperatures along the axial direction.

Deformable members can be used in the production of high-strength, ultra-thin wall expanded tubing and/or balloons (e.g., PTCA balloons for treating vascular disease with or without the use of stents/scaffolds). Ultra-thin walled tubing can be nested and bonded (e.g., with heat and pressure) to form multi-layer tubes with enhanced properties over single layered tubes of the same overall wall thickness (e.g., the sum of the wall thickness of the individual layers). Surface texturing on the outer diameter, inner diameter or both of the ultra-thin walled tubes created via the use of one or more deformable members can improve the bonding of the individual ultra-thin walled tubes to each other with or without the use of one or more tie layers between two or more of the ultra-thin walled tubes. Ultra-thin walled PTCA balloons can be used to achieve lower navigation profiles (e.g., smaller profiles for improved delivery to treatment sites) and crossing profiles (e.g., smaller profiles for passing through/crossing a diseased site/lesion) for PTCA and stent/scaffold delivery balloons.

Deformable members can aid in the continuous expansion of continuous (e.g., very long) lengths of input tubing. In preferred embodiments, tubing with an applied internal pressure and deformable member(s) translate relative to a heat source and a mold (e.g., a heated mold) or the heat source translates relative to the tubing and deformable member(s).

Deformable members can aid in the expansion of polymer tubes that are inherently difficult to expand uniformly due to inherent attributes and properties including, but not limited to, low molecular weight, low viscosity, low crystallinity, low glass transition temperature, low strength, low modulus, high tendency for deformation to be concentrated in small areas (e.g., necking), high tendency to deform/elongate preferentially along one or more axes, strong temperature-mechanical property correlations, and high dimensional and or property variation along one or more axes.

In a preferred embodiment, an expanded tube is produced with a surface texture on both the inner diameter and the outer diameter via the use of deformable members. Deformable members can be positioned inside and outside of a polymeric tube prior to radial expansion/deformation. The deformable members and polymer tube can be radially expanded, with or without any axial stretch, into a mold. At least a portion of the surface texture of the deformable members can be impressed/transferred into the inner diameter/surface and outer diameter/surface of the polymeric tube.

Any combination of deformable member number, type, size, and property, and polymeric tube number, type, size and property can be used to produce expanded polymeric tubes with one or more advantages compared to polymeric tubing produced according to the current art including, but not limited to, enhanced properties, property and/or dimensional uniformity, and added or enhanced surface features along one or more surfaces of the expanded polymer tubing.

EXPERIMENTAL

Example 1: A polymeric "input" tube comprising Purasorb PL38 (Corbion Purac, USA) with an inner diameter of approximately 0.019 inches and an outer diameter of approximately 0.0475 inches was obtained. A polymeric tubular deformable member comprising ePTFE with an inner diameter of approximately 0.050 inches, a wall thickness of approximately 0.006 inches, a density of approximately 0.58 g/cc, and an average internodal distance of approximately 29 microns was obtained. The PLLA input tube was inserted into the lumen of the ePTFE deformable member. The PLLA input tube and the ePTFE deformable member were inserted into a metallic mold with an inner diameter of approximately 0.123 inches. The mold was heated to approximately 88° C. in order to raise the temperature of the PLLA input tube to a temperature suitable for axial and radial expansion to induce axial and radial molecular orientation. The input tube was stretched in the axial direction by approximately 12% and then pressurized to approximately 40 bar at rate of approximately 5 bar/second to radially expand the input tube and the deformable member into the metallic mold. The mold, expanded PLLA tube, and expanded ePTFE deformable member were then cooled to approximately room temperature and then the pressure was reduced to atmospheric pressure. The expanded PLLA tube and expanded ePTFE deformable member were removed from the mold. The expanded ePTFE deformable member was measured to have an outer diameter of approximately 0.123 inches and a wall thickness of approximately 0.0018 inches. The expanded ePTFE deformable member was removed from the expanded PLLA tube. The expanded PLLA tube was measured to have an outer diameter of approximately 0.1195 inches and a wall thickness of approximately 0.0038 inches, corresponding to a final axial deformation of 7% and representing an axial contraction of approximately 5% upon radial expansion. The expanded ePTFE deformable member was characterized by scanning electron microscopy (SEM) and exhibited an average inner diameter internodal distance of 31 microns. The expanded PLLA tube was characterized by SEM and exhibited an outer surface with an impression/texture from the node-fibril morphology of the inner diameter of the expanded ePTFE deformable member with an average repeating characteristic of approximately 34 microns corresponding to the inner diameter internodal distance of the expanded ePTFE deformable member. The average water contact angle (Tantec CAM-PLUS) of the expanded PLLA tube was measured to be approximately 80 degrees while the average water contact angle of an expanded PLLA tube produced without the use of a deformable member (e.g. the "input" PLLA tube was radially expanded directly into the metallic mold) was approximately 77 degrees.

Example 2: The procedure of Example 1 was repeated using a PLLA polymeric "input" tube with an inner diameter of approximately 0.019 inches and an outer diameter of approximately 0.0475 inches, an ePTFE polymeric tubular deformable member with an inner diameter of approximately 0.050 inches, a wall thickness of approximately 0.006 inches, a density of approximately 0.75 g/cc, and an average internodal distance of approximately 23 microns, and a metallic mold with an inner diameter of approximately 0.123 inches. The expanded ePTFE deformable member was measured to have an outer diameter of approximately 0.123 inches and a wall thickness of approximately 0.002 inches. The expanded PLLA tube was measured to have an outer diameter of approximately 0.119 inches and a wall thickness of approximately 0.0038 inches, corresponding to a final axial deformation of 7% and representing an axial contraction of approximately 5% upon radial expansion. The expanded ePTFE deformable member was characterized by SEM and exhibited an average inner diameter internodal distance of approximately 20 microns. The expanded PLLA tube was characterized by SEM and exhibited an outer surface with an impression/texture from the node-fibril morphology of the inner diameter of the expanded ePTFE deformable member with an average repeating characteristic of approximately 23 microns corresponding to the inner diameter internodal distance of the expanded ePTFE deformable member. The average water contact angle of the expanded PLLA tube was measured to be approximately 84 degrees while the average water contact angle of an expanded PLLA tube produced without the use of a deformable member (e.g. the "input" PLLA tube was radially expanded directly into the metallic mold) was approximately 77 degrees.

Figure 9:
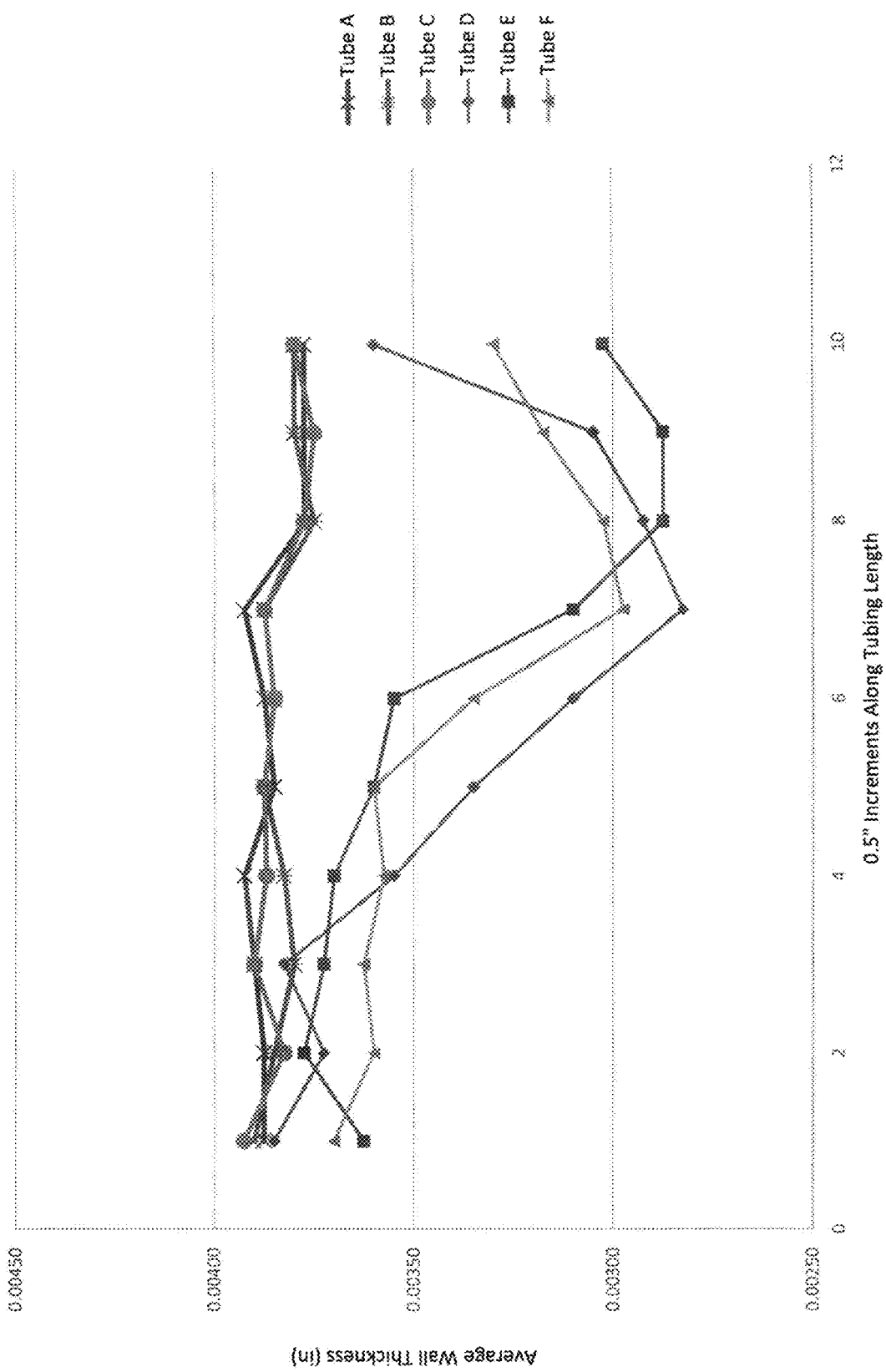
FIG. 9. provides average wall thickness data for PLLA tubes produced with and without the use of the method disclosed herein.

Example 3. The procedure of Example 1 was repeated using a PLLA polymeric "input" tube with an inner diameter of approximately 0.019 inches and an outer diameter of approximately 0.0475 inches, an ePTFE polymeric tubular deformable member with an inner diameter of approximately 0.050 inches, a wall thickness of approximately 0.006 inches, a density of approximately 0.58 g/cc, and an average internodal distance of approximately 29 microns, and a metallic mold with an inner diameter of approximately 0.123 inches and a length of approximately 4.5 inches. The mold was heated to approximately 85 C on the left side and to 88 C on the right side to create a condition of length-wise (axial) temperature non-uniformity for the PLLA input tubes. Expanded PLLA tubes A, B, and C were produced with the non-uniform temperature distribution and with the use of ePTFE deformable members according to the method disclosed herein. Expanded PLLA tubes D, E, and F were produced with the non-uniform temperature distribution but without the use of deformable members wherein the "input" PLLA tubes were radially expanded directly into the metallic mold. The average wall thickness was measured in 0.5 inch increments along the length of each tube using a wall micrometer (Mitutoyo Model #317-351) and is shown in FIG. 9. For the tubes expanded with the deformable members (tubes A, B, and C), the average wall thickness was 0.0038 inches and the standard deviation was 0.00005 inches. The average wall thickness for the left and right halves of tubes A, B, and C were 0.0039 inches and 0.0038 inches, respectively, representing a difference of only 0.0001 inches. For the tubes expanded without the deformable members (tubes D, E, and F), the average wall thickness was 0.0034 inches and the standard deviation was 0.00033 inches. The average wall thickness for the left and right halves of tubes D, E, and F were 0.0037 inches and 0.0031 inches, respectively, representing a difference of 0.0006 inches. The tubes expanded with the deformable members (tubes A, B, and C) had a 6-fold lower standard deviation for average wall thickness compared to the tubes expanded without the deformable members (tubes D, E, and F). In addition, the difference in the average wall thickness between the left half and right halves of the tubes expanded with the deformable members (tubes A, B, and C) was also 6-fold lower than the difference in the average wall thickness between the left half and right halves of the tubes expanded without the deformable members (tubes D, E, and F). This example illustrates the advantageous use of deformable members to control the wall thickness uniformity in the axial direction of expanded PLLA tubes, especially in relation to minimizing the effect of temperature non-uniformity on wall thickness uniformity.

Example 4: A polymeric "input" tube comprising Purasorb PLC9538 (Corbion Purac, USA) with an inner diameter of approximately 0.043 inches and an outer diameter of approximately 0.117 inches was obtained. A polymeric tubular deformable member comprising ePTFE with an inner diameter of approximately 0.120 inches, a wall thickness of approximately 0.006 inches, a density of approximately 0.43 g/cc, and an average internodal distance of approximately 25 microns was obtained. The PLC input tube was inserted into the lumen of the ePTFE deformable member. The PLC input tube and the ePTFE deformable member were inserted into a metallic mold with an inner diameter of approximately 0.258 inches. The mold was heated to approximately 82° C. in order to raise the temperature of the PLC input tube to a temperature suitable for axial and radial expansion to induce axial and radial molecular orientation. The input tube was stretched in the axial direction by approximately 25% and then pressurized to approximately 30 bar at rate of approximately 2 bar/second to radially expand the input tube and the deformable member into the metallic mold. The mold, expanded PLC tube, and expanded ePTFE deformable member were then cooled to approximately room temperature and then the pressure was reduced to atmospheric pressure. The expanded PLC tube and expanded ePTFE deformable member were removed from the mold. The expanded ePTFE deformable member was measured to have an outer diameter of approximately 0.258 inches and a wall thickness of approximately 0.0015 inches. The expanded ePTFE deformable member was removed from the expanded PLC tube. The expanded PLC tube had outer diameter surface characteristics corresponding to the node-fibril morphology of the expanded ePTFE deformable member. The expanded PLC tube was measured to have an outer diameter of approximately 0.255 inches and a wall thickness of approximately 0.0101 inches, corresponding to a final axial deformation of 20% and representing an axial contraction of approximately 5% upon radial expansion. The standard deviation of the average wall thickness measured at five discrete cross sections down the length of each of five expanded PLC tubes was approximately 0.00015 inches.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

What is claimed is:

1. A molecularly oriented polymeric tube, wherein the molecularly oriented polymeric tube exhibits a standard deviation of average wall thickness measured at discrete cross sections of the molecularly oriented polymeric tube that is about 9.7% or less of the overall average wall thickness of the molecularly oriented polymeric tube.

2. The molecularly oriented polymeric tube of claim 1, wherein the molecularly oriented polymeric tube exhibits a standard deviation of average wall thickness measured at discrete cross sections of the molecularly oriented polymeric tube that is less than 1.5% of the overall average wall thickness of the molecularly oriented polymeric tube.

3. The molecularly oriented polymeric tube of claim 1, wherein the molecularly oriented polymeric tube exhibits a standard deviation of average wall thickness measured at discrete cross sections of the molecularly oriented polymeric tube that is less than 1.0% of the overall average wall thickness of the molecularly oriented polymeric tube.

4. The molecularly oriented polymeric tube of claim 1, wherein the molecularly oriented polymeric tube exhibits a standard deviation of average wall thickness measured at discrete cross sections of the molecularly oriented polymeric tube that is less than 0.5% of the overall average wall thickness of the molecularly oriented polymeric tube.

5. The molecularly oriented polymeric tube of claim 1, wherein:
the discrete cross sections are measured at 10 or more locations down a length of the molecularly oriented polymeric tube, and
the distance between each of the 10 or more locations is at least 9% of a total length of the molecularly oriented polymeric tube.

6. The molecularly oriented polymeric tube of claim 5, wherein the length of the molecularly oriented polymeric tube is at least about 4 inches.

7. The molecularly oriented polymeric tube of claim 6, wherein the length of the molecularly oriented polymeric tube is at least about 8 inches.

8. The molecularly oriented polymeric tube of claim 6, wherein the molecularly oriented polymeric tube is converted into one or more stents by forming one or more stent patterns from the molecularly oriented polymeric tube.

9. The molecularly oriented polymeric tube of claim 8, wherein the one or more stents are formed from the molecularly oriented polymeric tube by laser cutting.

10. The molecularly oriented polymeric tube of claim 1, wherein the molecularly oriented polymeric tube has a surface corresponding to a surface characteristic of a deformable member used in connection with an expansion of a polymeric tube to obtain the molecularly oriented polymeric tube.

11. The molecularly oriented polymeric tube of claim 10, wherein the surface of the molecularly oriented polymeric tube corresponds to an impression from a morphology of the deformable member.

12. The molecularly oriented polymeric tube of claim 11, wherein the morphology of the deformable member corresponds to a node-fibril morphology of expanded polytetrafluoroethylene.

13. The molecularly oriented polymeric tube of claim 12, wherein the water contact angle ranges from about 80 degrees to about 85 degrees.

14. The molecularly oriented polymeric tube of claim 1, wherein the molecularly oriented polymeric tube is bioabsorbable.

15. The molecularly oriented polymeric tube of claim 14, wherein the molecularly oriented polymeric tube comprises one or more of a polyester, a poly α-hydroxy ester, a polyetherester, a polylactide, a polycaprolactone, a polyglycolide, a poly(dioxanone), a poly trimethylene carbonate, a poly(hydroxybutyrate), a poly(anhydride), an aliphatic polycarbonate, a poly(orthoester), a poly(amino acid), a poly (ethylene oxide), a poly (ethylene glycol), and stereoisomers, or copolymers or blends thereof.

16. The molecularly oriented polymeric tube of claim 1, wherein an average wall thickness of the molecularly oriented polymeric tube is less than 0.0040 inches.

17. The molecularly oriented polymeric tube of claim 16, wherein the average wall thickness is less than 0.0035 inches.

18. The molecularly oriented polymeric tube of claim 16, wherein the average wall thickness is less than 0.015 inches.

19. The molecularly oriented polymeric tube of claim 16, wherein an outside diameter of the molecularly oriented polymeric tube is less than about 0.5000 inches.

20. The molecularly oriented polymeric tube of claim 19, wherein the outside diameter of the molecularly oriented polymeric tube is about 0.255 inches or less.

21. The molecularly oriented polymeric tube of claim 19, wherein the outside diameter of the molecularly oriented polymeric tube is about 0.1195 inches or less.

22. The molecularly oriented polymeric tube of claim 1, wherein an outer surface of the molecularly oriented polymeric tube has a repeatable pattern imprinted thereon.

23. The molecularly oriented polymeric tube of claim 22, wherein the repeatable pattern has an average distance of about 34 micrometers or less between nodes.

24. The molecularly oriented polymeric tube of claim 1, wherein a contact angle of an outer surface of the molecularly oriented polymeric tube based at least in part on a deformable member in which a polymeric tube is expanded to obtain the molecularly oriented polymeric tube.

* * * * *